United States Patent [19]

Botvidsson

[11] Patent Number: 4,641,664
[45] Date of Patent: Feb. 10, 1987

[54] ENDOCARDIAL ELECTRODE ARRANGEMENT

[75] Inventor: Lars Botvidsson, Jaerfaella, Sweden

[73] Assignee: Siemens Aktiengesellschaft, Berlin and Munich, Fed. Rep. of Germany

[21] Appl. No.: 723,081

[22] Filed: Apr. 15, 1985

[30] Foreign Application Priority Data

Apr. 13, 1984 [DE] Fed. Rep. of Germany ....... 3414072

[51] Int. Cl.⁴ .............................................. A61N 1/04
[52] U.S. Cl. .................................. 128/785; 128/786; 128/642; 128/419 P
[58] Field of Search .............................. 128/783–786, 128/419 P, 639, 642

[56] References Cited

U.S. PATENT DOCUMENTS

| | | | |
|---|---|---|---|
| 3,902,501 | 9/1975 | Citron et al. | 128/419 P |
| 3,939,843 | 2/1976 | Smyth | 128/419 P |
| 4,026,303 | 5/1977 | Babotai | 128/419 P |
| 4,269,198 | 5/1981 | Stokes | 128/785 |
| 4,301,815 | 11/1981 | Doring | 128/786 |
| 4,407,303 | 10/1983 | Akerström | 128/786 |
| 4,409,994 | 10/1983 | Doring | 128/419 P |
| 4,432,377 | 2/1984 | Dickhudt | 128/786 |
| 4,465,079 | 8/1984 | Dickhudt | 128/785 |
| 4,506,679 | 3/1985 | Mann | 128/786 |
| 4,519,404 | 5/1985 | Fleischhacker | 128/419 P |
| 4,549,557 | 10/1985 | Hakki | 128/642 |

Primary Examiner—William E. Kamm
Assistant Examiner—Mitchell J. Shein
Attorney, Agent, or Firm—Hill, Van Santen, Steadman & Simpson

[57] ABSTRACT

An exemplary electrode arrangement comprises an elongated electrical conductor with a covering of electrical insulation and with an electrode head electrically connected to the distal end of the conductor for supplying stimulation pulses to the heart. The electrode arrangement includes a filamentary element or elements for fixing the conductor assembly to a cardiac wall. In order to be able to flatten the or each element closely against the conductor assembly and to anchor the electrode head securely in the trabeculae and to nonetheless facilitate a subsequent positional correction of the electrode head in the heart, it is inventively proposed that the or each filamentary element be of soft, flexible material and extend in a plane perpendicular to the axis of the conductor, the or each element preferably at least partially encircling the conductor assembly at a substantial spacing therefrom.

14 Claims, 7 Drawing Figures

ENDOCARDIAL ELECTRODE ARRANGEMENT

BACKGROUND OF THE INVENTION

The invention relates to an endocardial electrode arrangement for the intracardial stimulation of the heart, comprising an elongated electrical conductor with a covering of electrical insulation, and with an electrode head electrically connected to the distal end of the conductor and serving for the supply of stimulation pulses to the heart, and further comprising emplacement means secured to the electrode head or in proximity thereto for the fixation of the assembly to a wall of a cardiac cavity.

An endocardial electrode of this type is known from the U.S. Pat. No. 3,902,501. Serving as emplacement means given this electrode are tines of silicone rubber immediately behind the electrode head which engage into the trabeculae immediately after application and thus keep the electrode in place. It is intended that the tines be held against the insulation of the electrode when introduced into a vein.

U.S. Pat. No. 4,026,303 discloses an endocardial electrode which comprises an insulated, helical, stiff part at the electrode tip or on the insulation of the electrode lead near the electrode tip. This part serves the purpose of screwing and fixing the electrode in the trabeculae of the heart. The helix extends beyond the insulation and, due to the relatively thick helix, the resultant diameter of the electrode can be disturbingly large when introduced into a vein. The fixing of this electrode with the helical part is not as effective as the fixing of an electrode that is provided with tines.

SUMMARY OF THE INVENTION

The object of the invention is to provide an endocardial electrode of the type initially defined wherein the emplacement means can flatten closely against the electrode insulation and wherein the electrode can be securely and stably anchored in the trabeculae while a subsequent correction of position in the heart is nonetheless facilitated.

This object is achieved in accordance with the invention in that at least one filamentary element of soft, flexible material lying in a plane perpendicular to the axis of the conductor is provided for effecting fixation. When guiding the electrode through a vein, the or each filamentary element flattens closely against the insulation due to the material properties, so that the diameter of the electrode is kept small. The electrode can be securely anchored in the trabeculae due to the configuration of the or each filamentary element. Since the or each element projects perpendicularly to the axis of the conductor assembly, a subsequent positional correction of the electrode head can be easily carried out. When the electrode head is withdrawn from the trabeculae, the or each filamentary element is bent forward.

In a particularly advantageous development of the invention, it is proposed that the or each filamentary element at least partially encircles the conductor assembly at a substantial spacing. With such a normal or unconfined configuration of the emplacement means, it is achieved that the electrode can be readily screwed into the trabeculae. When the electrode is guided through a vein, the or each element of the fixation means flattens closely against the insulation in a roughly helical configuration.

It is proposed in an advantageous development of the invention that the filamentary element means in its unconfined configuration have a first length portion extending substantially in a plane at right angles to the axis of the electrode, and have a second length section extending from the first length section generally along a circular arc at a substantial distance from the conductor assembly. With this configuration, the spacing of the arcuate part of the filamentary element means is the same in all directions relative to the conductor assembly. By providing a plurality of filamentary elements with such arcuate parts, an even more secure anchoring in the trabeculae is achieved.

The invention shall be explained in greater detail with reference to a number of illustrative embodiments shown in the figures on the accompanying drawing sheet, and other objects features and advantages of the invention will be apparent from this detailed disclosure, taken in connection with the accompanying claims.

DETAILED DESCRIPTION

Figure 1:
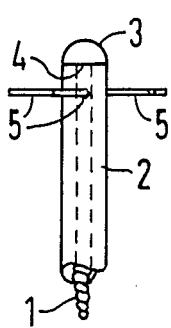
FIG. 1 is a side view of a distal end of an endocardial electrode according to the invention.

In FIG. 1, 1 indicates an electrical conductor of an electrode having a covering of an electrical insulation 2 and having an electrode head 3 electrically connected to the distal end of the conductor 1, to form a conductor assembly. The electrode head 3 is shown as being essentially cylindrical and rounded at its free end. The electrode head, however, can have different shapes, for example a cylindrical shape with a generally flat (non-rounded) end, or the like. At proximal end 4, the electrode head 3 may be flat and of the same external diameter as the insulation 2. After application of the electrode head 3 to a cardiac wall, stimulation pulses can be supplied to the heart via conductor 1 and electrode head 3. In order to fix the conductor assembly at its distal end, filamentary elements 5 of soft, flexible material are provided on the lead assembly 1, 2 or on the electrode head 3 of the conductor assembly.

Figure 2:
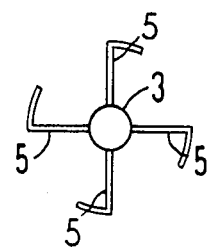
FIGS. 2-6 show plan views of endocardial electrodes with emplacement means of different configurations and comprised of different numbers of the filamentary elements.

FIGS. 1 and 2 show an electrode with four filamentary elements 5 which project from the external perimeter of the conductor assembly in respective different directions and all lying in a plane perpendicular to the axis of the conductor assembly.

Figure 3:
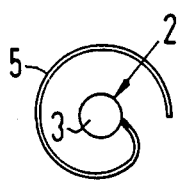

FIG. 3 shows a further illustrative embodiment having a single filamentary element 5 which partially encircles the electrode insulation 2 at a substantial distance therefrom and which lies in a plane perpendicular to the axis of the conductor assembly.

Figure 4:
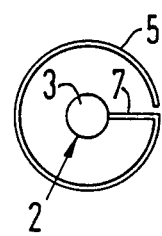

FIG. 4 shows a filamentary element 5 which has a first substantially straight length portion extending from the insulation 2 and a second length portion which extends from the first length portion in a circular arc at a substantial distance from the electrode insulation 2.

Figure 5:
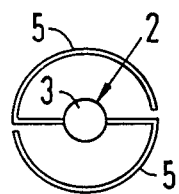
Figure 6:
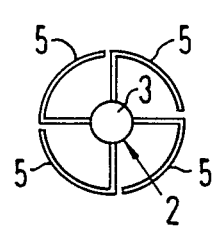

FIGS. 5 and 6 show a plurality of filamentary elements 5 extending from the electrode insulation 2. The filamentary elements 5 preferably include length portions extending substantially in circular arcs and together substantially completely encircling the conductor assembly. However, it is also possible to offset the filamentary elements axially of the conductor assembly, rather than all of the filamentary elements lying in a common plane at right angles to the electrode axis.

Figure 7:
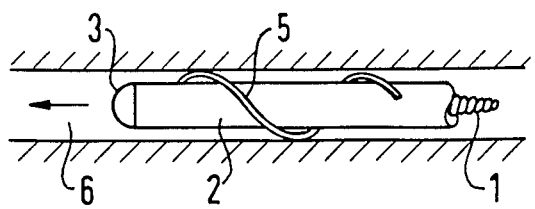
FIG. 7 is a side view of the distal portion of a conductor assembly as shown in FIG. 1 with a filamentary element such as illustrated in FIG. 3 or FIG. 4 held in its confined configuration during passage through a vein.

FIG. 7 shows how the filamentary element of FIG. 3 or FIG. 4 conforms closely against the electrode insulation 2 in a roughly helical configuration when the electrode is passed through a vein, so that the effective cross sectional area occupied by the electrode is kept small. After the passage of the distal end of the electrode through the vein, the filamentary element re-assumes its original shape such as shown in FIG. 3 or FIG. 4. The electrode head can then be screwed into the trabeculae with the assistance of the projecting resilient element or elements. This advantageous introduction through the vein and the subsequent screwing action is also realized with the configuration of filamentary elements 5 as shown in FIGS. 1, 2, 5 and 6.

If it is necessary to effect a positional correction of the electrode head, the distal portion of the electrode is withdrawn from the trabeculae. Since the filamentary elements 5 are disposed in a plane perpendicular to the axis of the conductor assembly and because of their soft, flexible material, they are readily deflected forwardly (or in the distal direction) when withdrawn. Subsequent corrections in the position of the electrode can be undertaken in a general fashion as a result of the unconfined configurations as shown in FIGS. 1 through 6.

As illustrated in FIG. 7, for each of the embodiments of FIGS. 1 to 6, the or each filamentary element 5 assumes a constricted configuration during passage through a vein 6 wherein the or each filamentary element lies closely adjacent the conductor assembly external perimeter throughout the length of such filamentary element, such filamentary element being retained in the constricted configuration solely by contact with the interior wall of the vein. When the or each filamentary element is no longer constricted by the interior wall of the vein, it re-assumes its respective non-restricted configuration as shown in FIGS. 1 to 6.

For each of the illustrated embodiments, the or each filamentary element extends for a distance from the exterior of the conductor assembly 1, 2, 3 which distance is of substantial extent in comparison to the maximum transverse dimension of the conductor assembly (at the plane of the filamentary elements) and which distance is substantially greater than a radial extent of the blood flow passage of vein 6, FIG. 7.

In the illustrated embodiment of FIGS. 1-2, the filamentary elements 5 re-assume the non-constricted configuration shown in FIG. 2 with radially extending parts and with tips extending arcuately at a distance from the external perimeter of the conductor assembly 1, 2, 3 which is at least substantially equal to the maximum transverse extent or diameter of the conductor assembly including the insulation covering at the plane of the filamentary elements.

In the illustrated embodiments of FIGS. 3-6, each filamentary element is shown as lying entirely in a plane perpendicular to the axis of the conductor assembly 1, 2, 3. In FIG. 3, in the non-constricted configuration, a first length portion extends generally perpendicularly from the axis and then curves in a circumferential direction to merge into a second length portion which encircles at least about 270 degrees of the external perimeter of the conductor assembly at a spacing from the exterior of the conductor assembly 1, 2, 3 at least substantially equal to the maximum transverse extent or diameter of the conductor assembly 1, 2, 3 (at the plane of the first length portion)..

In the unconstricted configurations of FIGS. 4, 5 and 6, a first length portion of each filamentary element such as indicated at 7 in FIG. 4, extends radially of the conductor assembly 1, 2, 3 over a distance of substantial extent in comparison to the maximum transverse dimension or diameter of the conductor assembly 1, 2, 3. In the illustrated embodiments, the second length portions extend along circular arcs at a distance from the exterior of the conductor assembly which is at least substantially equal to the maximum transverse extent or diameter of the conductor assembly 1, 2, 3. In FIG. 4, the second length portion of filamentary element 5 substantially completely encircles the conductor assembly, while in FIGS. 5 and 6, the second length portions together substantially completely encircle the conductor assembly.

With the filamentary element or elements of FIGS. 1-6 extending from the conductor assembly 1, 2, 3 in a plane perpendicular to the axis of the conductor assembly and with the filamentary elements having free ends, free of attachment to the conductor assembly, the electrode arrangement can be repositioned after fixation with minimum disturbance of the cardiac tissue. This results from an unconfined configuration of the filamentary elements in FIGS. 1-6 which is deflectible in either axial direction with essentially equal force applied to the conductor assembly (with the outer portions of the filamentary elements restrained), and wherein deflection of the filamentary elements in the distal direction is resisted by the unconfined configuration to an extent not exceeding the resistance to deflection in the proximal direction (when the conductor assembly is held against movement). In particular, with a force applied to the unconfined configuration parallel to the axis of the conductor assembly and in the distal direction, the filamentary elements of FIGS. 1-6 respond with essentially pure deflection, and no substantial component of the applied force acts to compress the length portions of the filamentary elements extending from the conductor assembly.

The filamentary elements of FIGS. 1-6 are of soft flexible material such that the elements are held in the confined configuration such as shown in FIG. 7 solely by the interior wall of vein 6 with minimal disturbance of such interior wall during passage of the electrode through the vein. Preferably the filamentary elements of FIGS. 1-6 exhibit the minimum resilient restoring force required to reliably return the elements to their unconfined configurations as shown in FIGS. 1-6 such resilient restoring force preferably being sufficient to restore the elements to their unconfined configurations as shown, in any orientation of the electrode relative to the earth's gravitational field.

In FIGS. 1-2 and FIGS. 4, 5 and 6, each of the filamentary elements may have a smooth curved configuration corresponding to that of the initial part of the filamentary element of FIG. 3, rather than having a first substantially straight radially extending portion joined with an arcuately extending portion at a distinct bend as shown. In such modified embodiments the same number of filamentary elements may be present as in the corresponding embodiment actually illustrated, and the overall lengths of the respective elements may be the same.

In each of the embodiments of FIGS. 1-6 and in each of the modifications of FIGS. 1-2 and FIGS. 4, 5 and 6 with smoothly curving filamentary element configurations, the emplacement means consists of filamentary elements of soft, flexible material such as, for example, silicon rubber, polyurethane or polyethylene. Due to the shape and length of such filamentary elements, they mold themselves tightly to the exterior of the conductor assembly 1, 2 in helical fashion when the electrode is introduced into a vein as shown in FIG. 7. As a result of the soft flexible material, the filamentary configuration, the non-confined shape, and the overall length or extent of the elements of the electrode emplacement means, the electrodes of the present invention, for introduction, require no retainer means such as is the case given the emplacement means of U.S. Pat. No. 3,902,501.

In each of the embodiments of FIGS. 1-6, and in each of the described modifications of FIGS. 1-2, and 4-6 based on FIG. 3, each of the filamentary elements has a sufficient extent as measured along the successive portions of the length thereof so as to be safely deflectable by the interior wall of the vein 6, FIG. 7, to lie closely adjacent the exterior of the conductor assembly as shown in FIG. 7 over the entire extent of such filamentary element during passage of the emplacement means with the electrode through the vein. Thus no retainer for the filamentary elements of the emplacement means is required.

It will be apparent that modifications and variations may be effected without departing from the scope of the teachings and concepts of the present invention.

I claim as my invention:

1. An endocardial electrode arrangement for intracardial stimulation of the heart comprising a conductor assembly having an axially elongated electrical conductor and a covering of electrical insulation and an electrode head electrically connected to a distal end of the electrical conductor for supplying stimulation pulses to the heart; and emplacement means secured to the conductor assembly in the vicinity of the distal end for fixing the conductor assembly to a cardiac wall, said emplacement means having at least one filamentary element of soft flexible material at least partially surrounding said conductor assembly spaced from said insulation end extending from the conductor assembly in a plane perpendicular to the elevated axis of the conductor assembly for fixing the conductor assembly to a cardiac wall, said filamentary element having a length so as to be safely deflectable by a wall of a blood vessel to a position closely adjacent the insulation of the conductor assembly during passage through a vein.

2. An endocardial electrode arrangement according to claim 1, wherein the filamentary element has a first length portion which is substantially straight and has a second length portion which extends from the first length portion in a circular arc spaced from the conductor assembly.

3. An endocardial electrode arrangement according to claim 1, wherein the filamentary element substantially completely encircles the conductor assembly.

4. An endocardial electrode arrangement according to claim 1, wherein the filamentary element has a first length portion extending away from the conductor assembly and has a second length portion extending from the first length portion and encircling more than one-half of the perimeter of the conductor assembly at a spacing therefrom greater than the transverse dimension of the conductor assembly.

5. An endocardial electrode arrangement according to claim 1, wherein said emplacement means comprises further a plurality of filamentary additional elements disposed around the conductor assembly.

6. An endocardial electrode arrangement according to claim 5, wherein each filamentary element partially encircles the conductor assembly spaced from the exterior of the conductor assembly.

7. An endocardial electrode arrangement according to claim 5, wherein each filamentary element has a first length portion which is substantially straight and has a second length portion which extends from the first length portion in a circular arc spaced from the conductor assembly.

8. An endocardial electrode arrangement according to claim 5, wherein each filamentary element partially encircles the conductor assembly.

9. An endocardial electrode arrangement according to claim 5, wherein each filamentary element has a first length portion extending away from the conductor assembly and has a second length portion extending from the first length portion and partially encircling the conductor assembly, the second length portions of the filamentary elements in combination encircling more than one-half of the perimeter of the conductor assembly at a spacing therefrom greater than the transverse dimension of the conductor assembly.

10. An endocardial electrode arrangement for introduction into a heart cavity through a vein and for subsequent fixation in the cavity, said arrangement comprising a conductor assembly having a distal end with a maximum transverse extent to permit passage of said conductor assembly through a vein and having an axially elongated electrical conductor having a covering of electrical insulation and having an electrode contact means for making electrical contact with a wall of a heart cavity upon fixation therein, said electrode contact means being electrically connected with said electrical conductor and being located in the vicinity of the distal end of the conductor assembly; and emplacement means secured to the conductor assembly in the vicinity of the distal end thereof for effecting said fixation of the conductor assembly, said emplacement means having filamentary element means disposed in a plane perpendicular to said elongated axis when in said heart and consisting of material having a resiliency selected for permitting said filamentary element means to be constricted into a helical configuration wrapped closely about the conductor assembly during insertion thereof through a vein and thereafter when clear of said vein for re-assuming an unconstricted configuration with a length portion thereof encircling more than one-half of the perimeter of the conductor assembly at a spacing from said conductor assembly at least equal to said maximum transverse extent and for permitting withdrawal of the conductor assembly without a resulting compressive component of force being exerted on the portion of the filamentary element means adjacent the exterior of the conductor assembly.

11. An endocardial electrode arrangement according to claim 10 wherein said length portion substantially encircles said conductor assembly.

12. An endocardial electrode arrangement according to claim 10, wherein said filamentary means comprises a plurality of individual filamentary elements disposed around the conductor assembly.

13. An endocardial electrode arrangement according to claim 12, wherein said resiliency of each of said filamentary elements is selected for permitting each filamentary element to be constricted into a helical configuration wrapped closely about the conductor assembly during insertion through a vein and thereafter when clear of such vein for re-assuming said unconstricted configuration with said respective length portions of said filamentary elements in combination encircling more than one-half of the perimeter of the conductor assembly at a spacing therefrom which is at least equal to said maximum transverse extent.

14. An endocardial arrangement according to claim 13, wherein said length portions in combination substantially completely encircle the conductor assembly when in said unconstricted configuration.

* * * * *